United States Patent [19]

Burzin et al.

[11] 4,359,588
[45] Nov. 16, 1982

[54] ODORIFEROUS ALIPHATIC ETHERS OF HYDROXYMETHYLCYCLODODECANE

[75] Inventors: Klaus Burzin; Werner Otte, both of Marl, Fed. Rep. of Germany

[73] Assignee: Chemische Werke Huels, Aktiengesellschaft, Marl, Fed. Rep. of Germany

[21] Appl. No.: 167,600

[22] Filed: Jul. 11, 1980

[30] Foreign Application Priority Data

Jul. 13, 1979 [DE] Fed. Rep. of Germany ....... 2928347

[51] Int. Cl.³ .................. C07C 43/115; C07C 43/162
[52] U.S. Cl. ................................. 568/579; 252/522 R
[58] Field of Search .............................. 568/670, 579; 252/522 R

[56] References Cited
U.S. PATENT DOCUMENTS 3,281,474 10/1966 Leidig ................................. 568/579
3,845,141 10/1974 Naegeli ............................... 568/579

Primary Examiner—Bernard Helfin
Attorney, Agent, or Firm—Millen & White

[57] ABSTRACT

Aliphatic ethers of hydroxymethylcyclododecane of the general formula

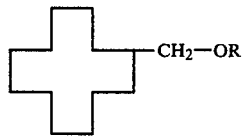

wherein R is a saturated or unsaturated aliphatic hydrocarbon residue of 1-4 carbon atoms, are valuable odoriferous substances possessing a long-lasting, intense woodsy scent with a balsam note of great richness.

6 Claims, No Drawings

ODORIFEROUS ALIPHATIC ETHERS OF HYDROXYMETHYLCYCLODODECANE

BACKGROUND OF THE INVENTION

The present invention relates to aliphatic ethers of hydroxymethylcyclododecane which have valuable odoriferous properties.

SUMMARY OF THE INVENTION

It is an object of this invention to provide new compounds having odoriferous properties.

Upon further study of the specification and appended claims, further objects and advantages of this invention will become apparent to those skilled in the art.

These objects have been attained by providing aliphatic ethers of hydroxymethylcyclododecane of the formula

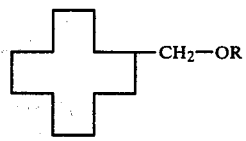

wherein R is a straight-chain or branched, saturated or unsaturated aliphatic hydrocarbon residue of 1-4 carbon atoms.

The compounds of this invention are novel odoriferous substances having an intense, long-lasting woodsy-balsam like scent. Moreover they have a very good capacity for being combined into novel scent nuances and possess an excellent fixative power.

DETAILED DISCUSSION

The ethers of this invention ordinarily can be prepared by etherification of hydroxymethylcyclododecane. In this connection, the conventional etherification methods described in the literature can be utilized. See, e.g., Houben-Weyl, "Methoden der organischen Chemie" (Methods of Organic Chemistry) VI/3, Oxygen Compounds I, part 3, pp. 10-137 (1965), whose disclosure is incorporated by reference herein.

The crude ethers so obtained are normally purified by fractional distillation. The removal of the final traces of unreacted alcohols is also possible using other separation methods, such as, for example, extraction or absorption processes.

The starting material hydroxymethylcyclododecane can be produced, for example, using conventional procedures and conditions by an oxo synthesis from 1,5,9-cyclododecatriene, carbon monoxide and hydrogen in the presence of specific catalysts known for such conventional prior art methods (see DAS's [German Published Applications] Nos. 1,211,174 and 1,668,255; U.S. Pat. No. 3,354,229; as well as French Pat. No. 1,438,811).

Typical representatives of the ethers of this invention include the cyclododecylmethyl-methyl-ether, the cyclododecylmethyl-ethyl-ether, the cyclododecylmethyl-isopropyl-ether, the cyclododecylmethyl-propenyl-ether, and the cyclododecylmethyl-allyl-ether. Among these, the methyl and ethyl ethers are the most preferred, since they are the compounds of most intense scent. As can be seen, any extent of branching and/or unsaturation (alkenyl or alkynyl) is possible in the R groups (e.g., sec-butyl, tert-butyl, sec-butenyl, isobutenyl, propargyl, butynyl, the unsaturation being in any position.

It is surprising that the aliphatic ethers of this invention, derived from the alcohol, hydroxymethylcyclododecane, which is readily accessible on a large industrial scale, are distinguished by an intense, typically woodsy scent with a balsam note of great richness and can be used for the production of valuable combinations and compositions, especially odoriferous substance compositions.

The ethers of this invention can be mixed with other compounds and materials, primarily with other odoriferous substances, in a great variety of quantitative ratios, to be determined in accordance with the finally desired odor, e.g., via routine preliminary tests, to obtain novel substance combinations and/or novel odoriferous substance compositions. In this connection, the proportion of the claimed ethers is generally up to 60% by weight, preferably 1-50% by weight.

Such odoriferous substance compositions include perfumes per se. They may also be used indirectly for the perfuming of cosmetics, such as, for example, creams, soaps, lotions, etc. Another possibility is the odor amelioration of industrial products, which otherwise possess an offensive odor, such as, for example, detergents and cleansing agents, disinfectants, textile assistants, etc.

The following examples explain the subject matter of the present invention in greater detail without, however, limiting the invention to these examples, since the other aliphatic ethers can be prepared in a corresponding way and likewise possess a typical woodsy scent with a balsam note.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Cyclododecylmethyl-methyl-ether 25 g (0.65 mol) of sodium amide was introduced into 150 ml of xylene and heated to boiling under agitation. Within one hour, 99 g (0.5 mol) of hydroxymethylcyclododecane, dissolved in 750 ml of xylene, was added dropwise to the boiling suspension. To complete the alcoholate formation the mixture was heated for another two hours under reflux. Thereafter 44 g (0.35 mol) of dimethyl sulfate was added dropwise. The reaction mixture was heated under reflux for another four hours and then poured into a mixture of ice and 35 g of sodium hydroxide. The organic phase was washed with water, dried with $Na_2SO_4$, and then distilled.

| Boiling Point: | 87–90° C. at 0.1 mbar |
|---|---|
| Yield: | 94% crude ether, 68% pure product |
| Refractive Index $n_{20}{}^D$: | 1.4751 |
| IR: | 1380 cm$^{-1}$, 1115 cm$^{-1}$ |
| NMR (CCl$_4$): | δ 3.19 (S) (CH$_3$—O), |

| | |
|---|---|
| δ 3.10 (D) (—CH₂—O—) | |

The cyclododecylmethyl-methyl-ether exhibits an intensive, pleasant wood scent.

EXAMPLE 2

Cyclododecylmethyl-ethyl-ether

The cyclododecylmethyl-ethyl-ether was obtained in correspondence with the statements in Example 1 by reacting 99 g of hydroxymethylcyclododecane with 54 g (0.35 mol) of diethyl sulfate.

| Boiling Point: | 105–110° C. at 0.2 mbar |
|---|---|
| Yield: | 92% crude ether, |
|  | 62% pure product |
| Refractive Index $n_{20}^D$: | 1.4720 |
| IR: | 1380 cm⁻¹, 1120 cm⁻¹ |
| NMR (CCl₄): | δ 3.35 (Q) (O—CH₂—CH₃), |
|  | δ 3.15 (D) (—CH₂—O—C₂H₅) |

The cyclododecylmethyl-ethyl-ether possesses a pleasant, intensive wood scent.

EXAMPLE 3

Cyclododecylmethyl-isopropyl-ether

According to the disclosure of Example 1, 99 g of hydroxymethylcyclododecane was first converted into the sodium alcoholate. 74 g (0.6 mol) of 2-bromopropane was added dropwise to the boiling suspension, and then the mixture was heated for 30 hours under reflux. The reaction mixture was poured into water, the organic phase was washed with water, dried over Na₂SO₄, and then distilled.

| Boiling Point: | 110–112° C. at 0.3 mbar |
|---|---|
| Yield: | 89% crude ether, |
|  | 79% pure product |
| Refractive Index $n_{20}^D$: | 1.4814 |
| IR: | 1370 cm⁻¹, 1357 cm⁻¹, |
|  | 1120 cm⁻¹ |
| NMR (CDCl₃): | δ 3.40 (Hept.) CH(CH₃)(CH₃) |
|  | δ 3.20 (D) (CH₂—O—C₃H₇) |

The cyclododecylmethyl-isopropyl-ether exhibits a wood scent.

EXAMPLE 4

Cyclododecylmethyl-allyl-ether

The cyclododecylmethyl-allyl-ether was prepared according to the data in Example 1 and Example 3, using in place of 2-bromopropane 73 g (0.6 mol) of 1-bromo-2-propene. The reaction mixture was heated under reflux for 24 hours, then poured into water, washed with water, dried over Na₂SO₄, and distilled.

| Boiling Point: | 115–118° C. at 0.2 mbar |
|---|---|
| Yield: | 88% crude ether, |
|  | 79% pure product |
| Refractive Index $n_{20}^D$: | 1.4812 |
| IR: | 1640 cm⁻¹, 1100 cm⁻¹, |
|  | 990 cm⁻¹, 910 cm⁻¹ |
| NMR (CCl₄): | δ 3.82 (D) (O—CH₂—CH=CH₂), |
|  | δ 3.15 (D) (—CH₂—O—CH₂CH=CH₂) |

The cyclododecylmethyl-allyl-ether possesses a pleasant wood scent.

Examples for odoriferous substance compositions containing the substances of this invention will be set forth below:

EXAMPLE 5 (Wood Base)

| | Parts by Weight |
|---|---|
| Cyclododecylmethyl-methyl-ether | 250 |
| Cyclododecylmethyl-ethyl-ether | 200 |
| Cyclocodecylmethyl-allyl-ether | 50 |
| "Oryclon" (Haarmann + Reimer) | 100 |
| Vetiveryl acetate | 100 |
| "Isoraldein 70" (L. Givaudan) | 50 |
| Guaiyl acetate | 50 |
| Cedar ketone (Haarmann + Reimer) | 100 |
| Phenylethyl alcohol | 50 |
| Coumarin | 50 |
| | 1,000 |

EXAMPLE 6 (Soap Perfume)

| | Parts by Weight |
|---|---|
| Cyclododecylmethyl-methyl-ether | 200 |
| Cyclododecylmethyl-ethyl-ether | 75 |
| Cyclododecylmethyl-isopropyl-ether | 75 |
| Methyl anthranilate | 100 |
| Bergamot oil | 70 |
| Balsam of Tolu | 25 |
| Indole | 5 |
| Limonene | 450 |
| | 1,000 |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An aliphatic ether of hydroxymethylcyclododecane of the formula

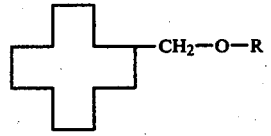

wherein R is a saturated or unsaturated aliphatic hydrocarbon residue of 1–4 carbon atoms.

2. Cyclododecylmethyl-methyl-ether, a compound of claim 1.

3. Cyclododecylmethyl-ethyl-ether, a compound of claim 1.

4. Cyclododecylmethyl-isopropyl-ether, a compound of claim 1.

5. Cyclododecylmethyl-propenyl-ether, a compound of claim 1.

6. Cyclododecylmethyl-allyl-ether, a compound of claim 1.